United States Patent
Melosh et al.

(10) Patent No.: US 11,255,853 B1
(45) Date of Patent: Feb. 22, 2022

(54) MULTI-ANALYTE MOLECULARLY IMPRINTED POLYMER SENSOR

(71) Applicant: Rhythmic Health, Inc., San Francisco, CA (US)

(72) Inventors: Nicholas Alexander Melosh, Menlo Park, CA (US); Marc Daniel Ferro, Oakland, CA (US); Benjamin Roth Lowenstein, San Francisco, CA (US); Paul Michael Litvak, San Francisco, CA (US)

(73) Assignee: Rhythmic Health, Inc., San Francisco, CA (US)

( * ) Notice: Subject to any disclaimer, the term of this patent is extended or adjusted under 35 U.S.C. 154(b) by 0 days.

(21) Appl. No.: 17/031,788

(22) Filed: Sep. 24, 2020

(51) Int. Cl.
  *G01N 33/543* (2006.01)
  *G01N 33/487* (2006.01)

(52) U.S. Cl.
  CPC . *G01N 33/54373* (2013.01); *G01N 33/48707* (2013.01); *G01N 2333/4737* (2013.01); *G01N 2333/52* (2013.01); *G01N 2600/00* (2013.01)

(58) Field of Classification Search
  CPC ..... G01N 33/54373; G01N 2333/4737; G01N 2333/52; G01N 2600/00; G01N 33/48707
  See application file for complete search history.

(56) References Cited

U.S. PATENT DOCUMENTS

| | | | |
|---|---|---|---|
| 2003/0113713 A1* | 6/2003 | Glezer | G01N 33/54373 435/5 |
| 2012/0118751 A1* | 5/2012 | Cai | G01N 33/54346 205/122 |
| 2014/0015548 A1* | 1/2014 | Naughton | G01N 27/3278 324/658 |
| 2016/0018347 A1* | 1/2016 | Drbal | A61M 1/28 210/647 |
| 2017/0050175 A1* | 2/2017 | Farr | B01J 20/268 |
| 2017/0079566 A1* | 3/2017 | Rong | A61B 5/14865 |
| 2018/0355089 A1* | 12/2018 | Ethirajan | G01N 33/53 |

FOREIGN PATENT DOCUMENTS

WO   WO 2019/173572 A1   9/2019

OTHER PUBLICATIONS

Heikenfeld, J. et al., "Accessing analytes in biofluids for peripheral biochemical monitoring," Nature Biotechnology, vol. 37, Apr. 2019, pp. 407-419.

(Continued)

*Primary Examiner* — Melanie Brown
(74) *Attorney, Agent, or Firm* — Fenwick & West LLP

(57) ABSTRACT

A multi-analyte sensor includes a body having a proximal end and a distal end. A plurality of strips is connected to one end of the body and a plurality of electrical conductors run through the body and into the plurality of strips. Exposed portions of first and second electrical conductors running through first and second strips are coated with analyte-responsive materials, such as a first molecular imprinted polymer (MIP) and a second MIP, respectively. The first MIP has binding sites for a first target analyte and the second MIP has binding sites for a second target analyte. The multi-analyte sensor may be part of a sensing device that also includes a controller and a data store.

20 Claims, 8 Drawing Sheets

(56) References Cited

OTHER PUBLICATIONS

Parlak, O. et al., "Molecularly selective nanoporous membrane-based wearable organic electrochemical device for noninvasive cortisol sensing," Science Advances, vol. 4, Jul. 20, 2018, pp. 1-10.
Saylan, Y. et al., "Molecularly Imprinted Polymer Based Sensors for Medical Applications," Sensors 19(6), Mar. 13, 2019, pp. 1-19.
Vasapollo, G. et al., "Molecularly Imprinted Polymers: Present and Future Prospective," International Journal of Molecular Sciences, vol. 12, Sep. 14, 2011, pp. 5908-5945.

* cited by examiner

MULTI-ANALYTE MOLECULARLY IMPRINTED POLYMER SENSOR

BACKGROUND

The subject matter described generally relates to sensors and, in particular, to a monolithic molecularly imprinted polymer (MIP) sensor for multiple analytes.

Personalized medicine aims to provide medical diagnostics and treatment to people based on their individual characteristics. In pursuit of this goal, a range of devices and sensors have been developed that enable people to collect physiological data at home without the need for a medical professional to be present. Many households also now have reliable, high-speed connections to the internet, allowing this data to be provided to a remote facility for analysis almost immediately, and the results of that analysis can be returned just as fast. According to some projections, personalized medicine will become a trillion-dollar industry in the next few years. Thus, there is significant demand for low-cost, convenient ways for people to collect physiological data.

SUMMARY

In various embodiments, a multi-analyte sensor includes multiple electrical conductors running through the body of a cable (e.g., forming a set of electrical lines). One end of the cable connects to a controller (e.g., via an adaptor) while the other end of the cable splits into multiple strips. Each strip has one or more of the electrical conductors running through it. Portions of the electrical conductors are exposed by openings in the strips. The exposed portions of the electrical conductors in each strip (except for one or more strips that are used for reference lines) are coated with a molecularly imprinted polymer (MIP). In one embodiment, the exposed portions of each strip are coated in a different MIP, with each MIP having binding sites for a corresponding target analyte. For example, one strip may have a MIP that has binding sites for cortisol while another strip may have a MIP with binding sites for testosterone. Thus, because the electrical properties (e.g., impedance) of the electrical circuit formed by a MIP-coated conductor and one or more reference lines will change depending on the amount of the target analyte bound to the binding sites of the MIP, each strip can provide a measure of the concentration of the corresponding analyte present in a sample to which the sensor is exposed.

DETAILED DESCRIPTION

The figures and the following description describe certain embodiments by way of illustration only. One skilled in the art will readily recognize from the following description that alternative embodiments of the structures and methods may be employed without departing from the principles described. Wherever practicable, similar or like reference numbers are used in the figures to indicate similar or like functionality. Where elements share a common numeral followed by a different letter, this indicates the elements are similar or identical. A reference to the numeral alone generally refers to any one or any combination of such elements, unless the context indicates otherwise.

Example System

Figure 1:
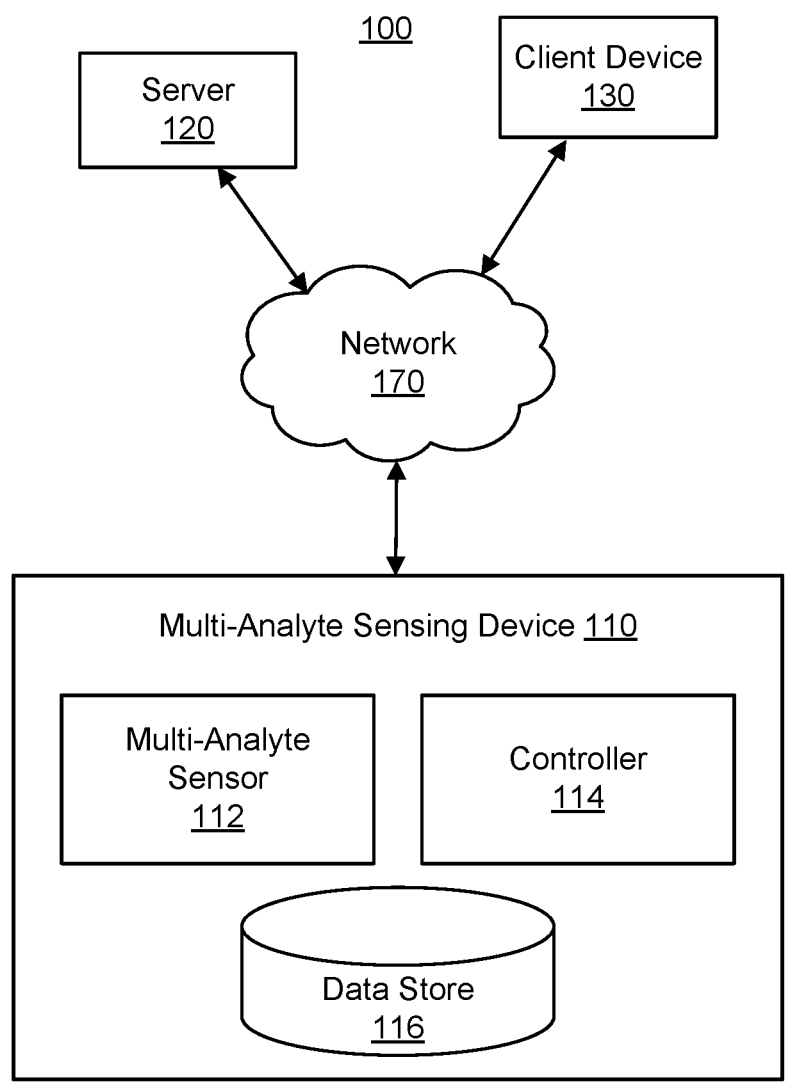
FIG. 1 is a block diagram of a networked computing environment including a sensing device with a multi-analyte sensor, according to one embodiment.

FIG. 1 illustrates one embodiment of a networked computing environment 100. In the embodiment shown, the networked computing environment 100 includes a multi-analyte sensing device 110, a server 120, and a client device 130, all connected via a network 170. In other embodiments, the networked computing environment 100 includes different or additional elements. In addition, the functions may be distributed among the elements in a different manner than described. For example, in some embodiments, the multi-analyte sensing device 110 may not have network connectivity and the server 120, client device 130, and network 170 may be omitted.

The multi-analyte sensing device 110 measures the concentration of two or more analytes in a biological sample from a user. The multi-analyte sensing device 110 may obtain the sample passively while the user is using the device for another task. For example, the multi-analyte sensing device 110 may be a toothbrush that measures the concentration of analytes in the user' saliva while the user is brushing their teeth. Similarly, the multi-analyte sensing device 110 may be an oral thermometer that measures analyte concentrations in saliva or a wearable device that measures analyte concentrations in sweat. In a less passive example, the user may provide a blood or urine sample either directly or indirectly into a sampling chamber or vessel of the multi-analyte sensing device 110.

In the embodiment shown in FIG. 1, the multi-analyte sensing device 110 includes a multi-analyte sensor 112, a controller 114, and a data store 116. The multi-analyte sensor 112 is a sensor configured to measure the concentration of two or more analytes in biological samples to which it is exposed. Embodiments of the multi-analyte sensor 112 are described in greater detail below, with reference to FIGS. 2 and 3. The controller 114 includes a processor or other circuitry that receives and processes signals from the multi-analyte sensor 112. The controller 114 may store measurements derived from the signals received from the multi-analyte sensor 112 in the data store 116 or send them via the network 170 to the server 120 or client device 130.

The server 120 and client device 130 are computer systems that may store and analyze measurements provided by the multi-analyte sensing device 110. In one embodiment, the server 120 receives measurements of analyte concentrations from the multi-analyte sensing device 110 and tracks variations in the concentrations over time. The server 120 correlates the variations with one or more health conditions and provides information regarding those health conditions to the client device 130 for display to the user. For example, a sudden spike in cortisol levels indicates acute stress and the user may be advised to undertake relaxation exercises (e.g., deep breathing) whereas consistently high level of cortisol indicates chronic stress and the user might be advised to consider a dietary supplement such as ashguawanda or a lifestyle change.

The network 170 provides the communication channels via which the other elements of the networked computing environment 100 communicate. The network 170 can include any combination of local area and/or wide area networks, using both wired and/or wireless communication systems. In one embodiment, the network 170 uses standard communications technologies and/or protocols. For example, the network 170 can include communication links using technologies such as Ethernet, 802.11, worldwide interoperability for microwave access (WiMAX), 3G, 4G, 5G, BlueTooth, BlueTooth Low Energy (BLE), Long Range Radio (LoRa), code division multiple access (CDMA), digital subscriber line (DSL), etc. Examples of networking protocols used for communicating via the network 170 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 170 may be represented using any suitable format, such as hypertext markup language (HTML) or extensible markup language (XML). In some embodiments, all or some of the communication links of the network 170 may be encrypted using any suitable technique or techniques.

Example Sensors

Figure 2A:
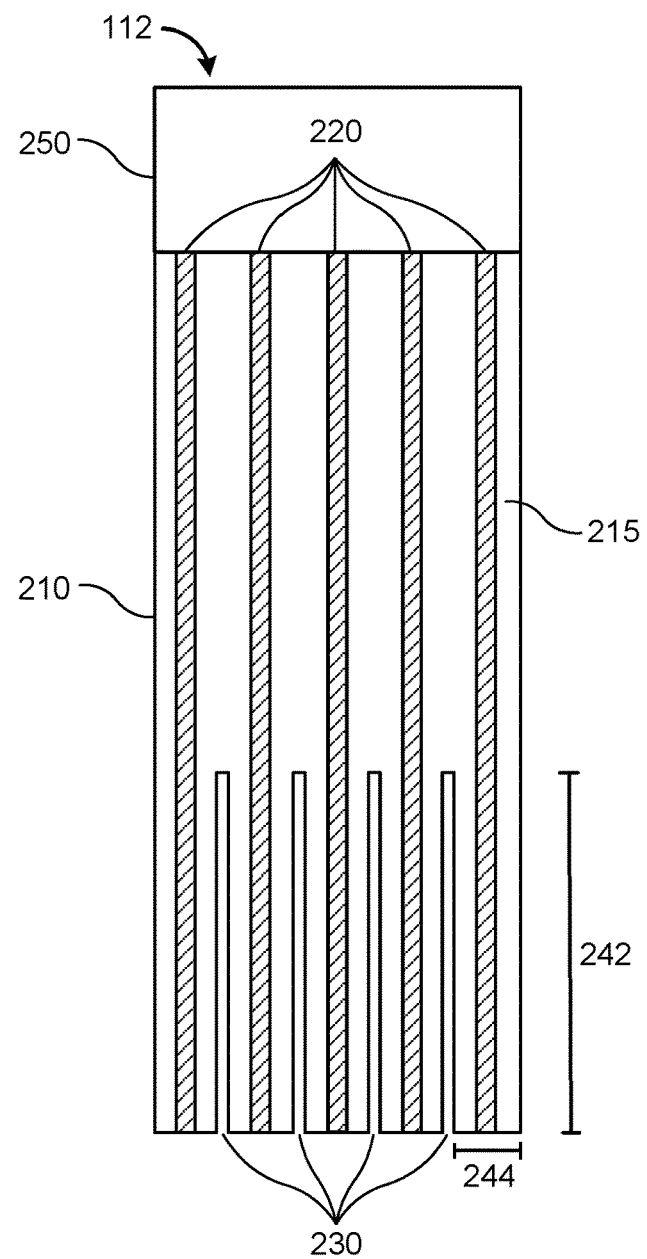
FIGS. 2A and 2B illustrate a first embodiment of the multi-analyte sensor of the sensing device.
Figure 2B:
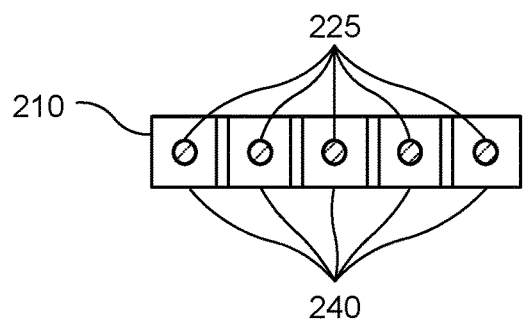

FIGS. 2A and 2B are schematic illustrations of one embodiment of the multi-analyte sensor 112. FIG. 2A a top-down view of the multi-analyte sensor 112 and FIG. 2B is an end-on view of the multi-analyte sensor 112. FIGS. 2A and 2B are not to scale but rather are drawn to illustrate the principles of the design of the multi-analyte sensor 112. In the description that follows, it is assumed that the multi-analyte sensor 112 is a MIP sensor in which exposed electrodes are coated in MIPs. However, different or additional types of analyte-responsive sensors may also be included in the multi-analyte sensing device 110. For example, some or all of the exposed electrodes may have a coating including antibodies, aptamers, or any other chemical-capture agent that includes binding sites that preferentially bind to target analytes.

A MIP is a polymer material that has binding sites with a strong affinity for a target analyte. The MIP is formed by polymerizing monomers in the presence of a template (which is often the target analyte). The monomers polymerize around some or all of the template. Thus, when the template is removed, a cavity is left behind that has a size, shape, and charge distribution that corresponds to the target analyte. Thus, when the MIP is exposed to the target analyte, molecules of the target analyte tend to bind to the MIP (similar to how antibodies bind to an antigen). Generally, the higher the concentration of the target analyte, the greater the number of molecules will bind to the MIP. MIP sensors detect the concentration of the corresponding target analyte by measuring changes in electrical properties of the sensor as molecules of the target analyte bind to the binding sites. For example, the impedance of a circuit including one class of MIP decreases as the number of molecules of the target analyte bound to the MIP increases, and thus the impedance decreases as the concentration of the target analyte increases. For another class of MIP, the impedance of the circuit increases as target molecules bind to the MIP, and thus the impedance increases with the concentration of the target analyte.

The multi-analyte sensor 112 shown in FIGS. 2A and 2B includes a cable 210, such as a flat flex cable (FFC) or ribbon cable with a zero insertion force (ZIF) connector, but any suitable configuration of conductors on or within an insulating substrate may be used. At one end of the cable 210, an adaptor 250 enables the multi-analyte sensor 112 to be connected to the controller 114. The adaptor 250 may clip into a socket (e.g., mounted on a printed circuit board inside the device 110 or on an exterior housing of the device) to allow relatively easy replacement of the sensor. Multiple electrical lines 220 made from an electrical conductor run from the adaptor 250 along the length of the cable 210 and to the other end, embedded within an insulating material. At the end of the cable 210 opposite the adaptor 250, a set of splits 230 divides the cable into strips 240. Thus, the cable 210 may be viewed as having a body 215 with electrical lines 220 running through a monolithic cable and the strips 240, where the monolithic cable separates into multiple parts, each having one or more of the electrical lines 220 running through it.

In FIG. 2A, the cable 210 has four longitudinal splits 230 (e.g., gaps or cuts) forming five strips 240, but the sensor 112 may have any number of strips limited only by the number of lines 220 in the cable. Similarly, each strip 240 is shown as including a single electrical line 220, but the strips may include any number of electrical lines. All of the strips 240 may have the same number of electrical lines 220 (e.g., one line, two lines, . . . , n lines) or the strips may include different numbers of lines (e.g., two subsets might have one line and three subsets might have two lines while a further subset has three lines, etc.). In one embodiment, the strips 240 have a length 242 between five microns and twenty centimeters and a width 244 between one micron and five centimeters. Similarly, the splits 230 may have a width between one micron and two centimeters. Alternatively, the strips 240 may abut directly against each other. The length 242 and width 244 of each strip 240 (and the length and width of each split 230) may be the same or different.

At the ends of the strips 240, portions 225 of the electrical lines 220 are exposed by an opening in the strip. In various embodiments, one or more of the strips 240 provide reference lines (e.g., the exposed portions 225 have no coating or have been treated to have substantially invariant electrical properties regardless of the presence of target analytes). The exposed portions 225 of the electrical lines 220 of the remaining strips 240 are coated with a MIP for a target analyte. Example target analytes that can be detected using MIP sensors include cortisol, dehydroepiandrosterone (DHEA), melatonin, progesterone, estrogen, testosterone, cytokines, C-reactive protein, and cholesterol, among many others. In one embodiment, each strip 240 (other than those that have reference lines) is configured to detect a different analyte and the exposed portion or portions 225 of the electrical lines 220 are coated in a MIP for detecting the corresponding analyte. Alternatively, some or all of the target analytes may have multiple strips 240 with exposed ends 225 coated in the corresponding MIP.

Regardless of the precise configuration of strips 240 and MIP coatings, if the exposed ends 225 of the multi-analyte sensor 112 are exposed to a sample, changes in the sensor's electrical properties may be used to detect the concentration of the target analytes in the sample. The target analytes selectively bond to the corresponding MIPs, which in turn change the electrical properties of the circuits formed by the corresponding electrical lines 220 and the reference line (or lines). For example, as the concentration of a target analyte increases, a greater number of target analyte molecules bind to the MIP for that analyte, and the impedance between a corresponding electrical line 220 and reference line decreases. The multi-analyte sensor 112 may be calibrated to convert measured impedance values into concentrations. Additionally or alternatively, variations in the capacitance, inductance, resistance, or any other electrical property may be measured and calibrated to provide a measure of the concentration of a target analyte in the sample. Example methods for calibrating the multi-analyte sensor 112 are described in greater detail below, with reference to FIGS. 5A and 5B.

Figure 3A:
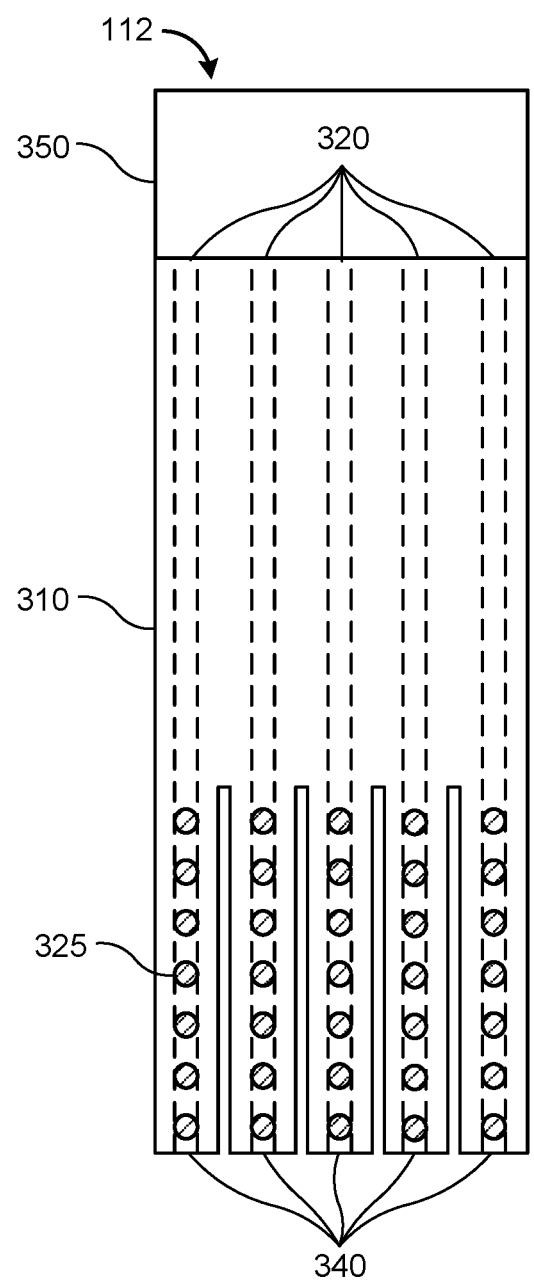
FIGS. 3A, 3B, and 3C illustrate a second embodiment of the multi-analyte sensor of the sensing device.
Figure 3B:
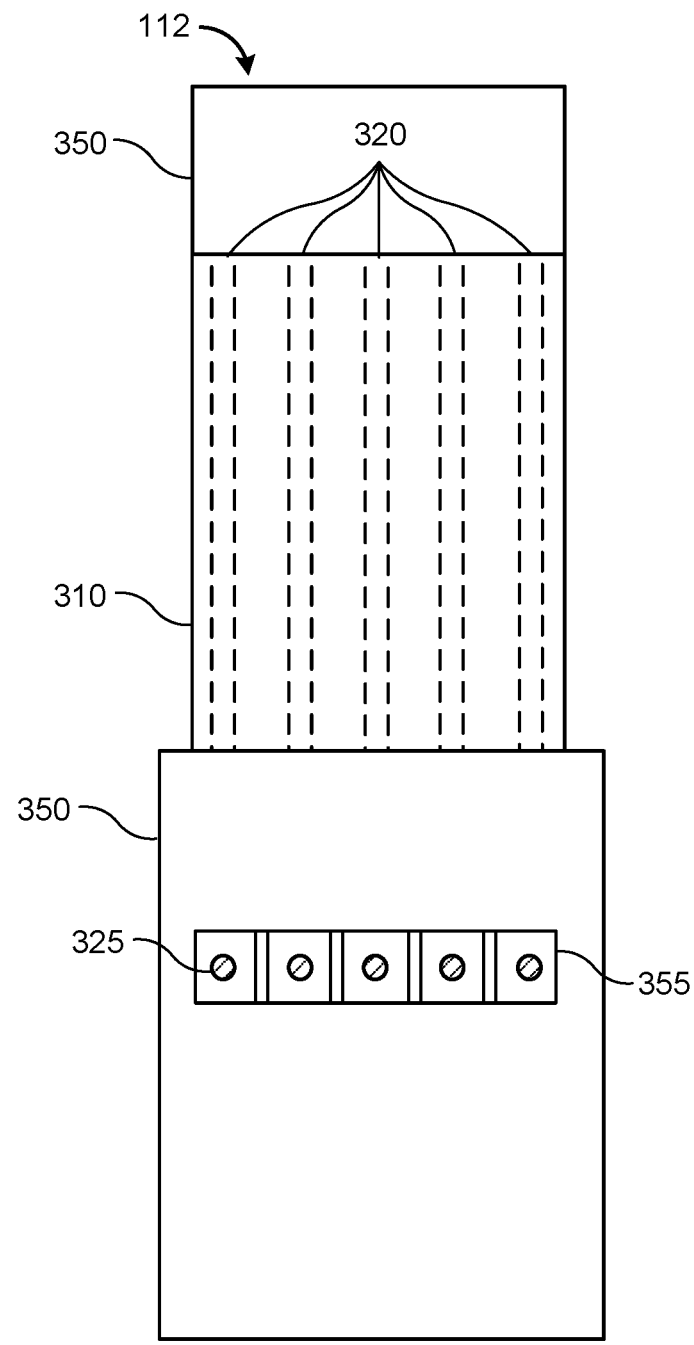

FIGS. 3A and 3B illustrate another embodiment of the multi-analyte sensor 112. Like the embodiment shown in FIGS. 2A and 2B, the embodiment shown in FIGS. 3A and 3B includes a cable 310 that has an adaptor 350 at one end and is split into multiple strips 340 at the other end. The cable 310 has multiple electrical lines 320 that run from the adaptor 350 at one end to the opposite end, which is divided into strips 340 (in the example shown, there are five strips, but the sensor cable 210 may be divided into any number of strips limited only by the number of lines in the cable).

In contrast to the embodiment shown in FIGS. 2A and 2B, the embodiment shown in FIGS. 3A and 3B has a set of holes 325 in the top (or bottom) surface of each strip 340 rather than (or in addition to) the end of each electrical line 320 being exposed. Each hole 325 exposes a portion of the electrical line 320 within the cable 310. As illustrated in FIG. 3B, a mask 350 can be placed on or over the cable 310. The mask 350 includes a window 355 that exposes one of the holes 325 of each electrical line 320. The mask 350 can be slid along the cable 310 to expose different holes 325. Thus, a set of holes 325 may be used to measure concentrations of the target analytes one or more times until the sensor's performance becomes degraded (e.g., due to the accumulation of contaminants on the exposed portions of the electrical lines 320) and then the mask 350 may be moved and a different set of holes used for measurements. This may extend the lifetime of the sensor 112. One skilled in the art will recognize other ways in which portions of electrical lines may be selectively exposed, such as periodically cutting off segments of the strips.

Figure 3C:
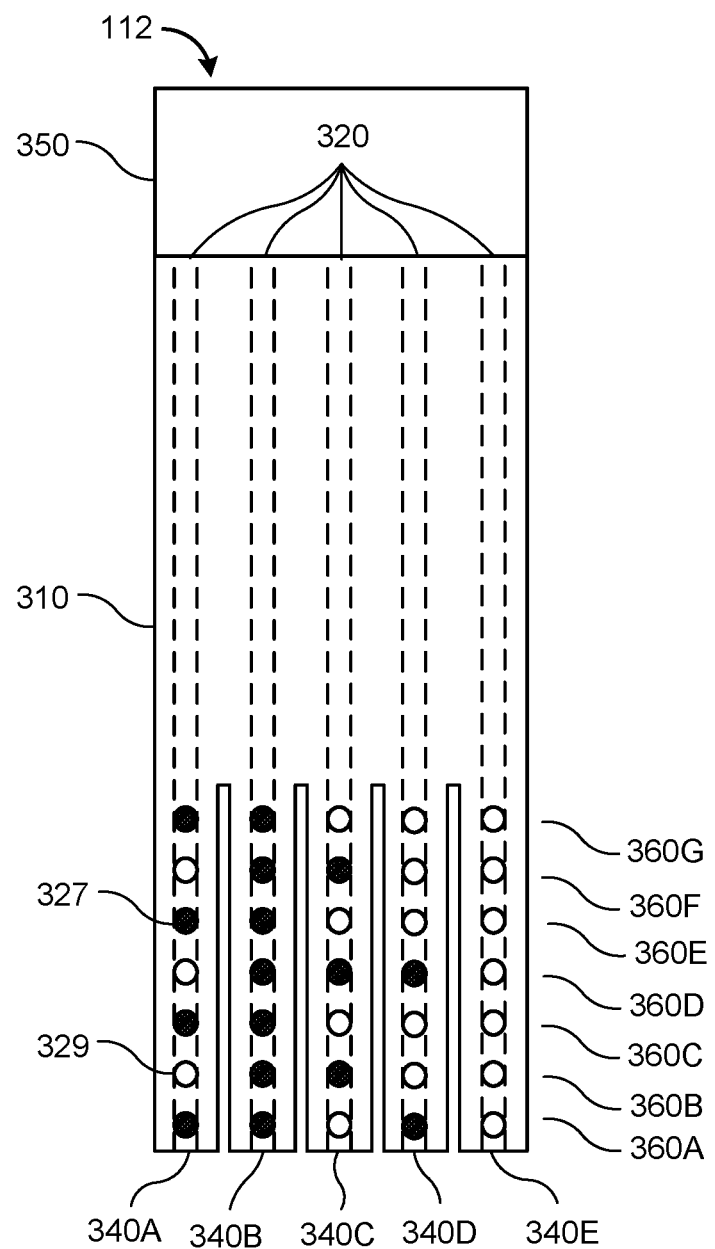

FIG. 3C illustrates a variation of the embodiment of the multi-analyte sensor 112 shown in FIGS. 3A and 3B that enables different subsets of the target analytes to be measured at different times. The illustrated multi-analyte sensor 112 has five strips 340A-E, each with seven holes 325 in rows 360A-G. Some of the holes are coated in a MIP (e.g., hole 327) while other holes (e.g., hole 329) are not. A measurement is made using a single row 360 (e.g., using a mask 355 as shown in FIG. 3B or another suitable technique). Consequently, the measurement provides a measure of target-analytes for which the hole on the corresponding strip 340 is coated in the MIP. Thus, different measurements can include values for the concentrations of different subsets of the target analytes.

The example sensor 112 shown in FIG. 3C is designed for taking one measurement a day over a one-week period. Each of the seven rows 360 corresponds to a different day. The first strip 340A includes holes coated in a MIP for a first target analyte in the first row 360A, third row 360C, fifth row 360E, and seventh row 360G. However, the holes in the second row 360B, fourth row 460D, and sixth row 460F are not coated in the MIP and thus the surface of the conductor remains directly exposed to the environment of sensor 112. Thus, the concentration of the first target analytes is measured every other day during the week. In contrast, the second strip 340B has all seven holes coated in a MIP for a second target analyte. Thus, the concentration of the second target analyte is measured daily. The third strip 340C includes holes coated in a MIP for a third target analyte in the second row 360B, fourth row 360D, and sixth row 360F. Thus, the concentration of the third target analyte is measured on the days that the first target analyte is not measured.

The fourth strip 340D includes holes coated in a MIP for a fourth target analyte in the first row 360A and the fourth row 360D. Thus, the concentration of the fourth target analyte is measured twice during the week. Finally, the fifth strip 340E includes no coated holes and provides a reference line. It should be understood that different numbers of strips 340 may be included along with a range of configurations of coated holes 327 and uncoated holes 329, depending on the target analytes and desired schedule for measurement of each target analyte.

Example Method of Manufacturing a Multi-Analyte Sensor

Figure 4A:
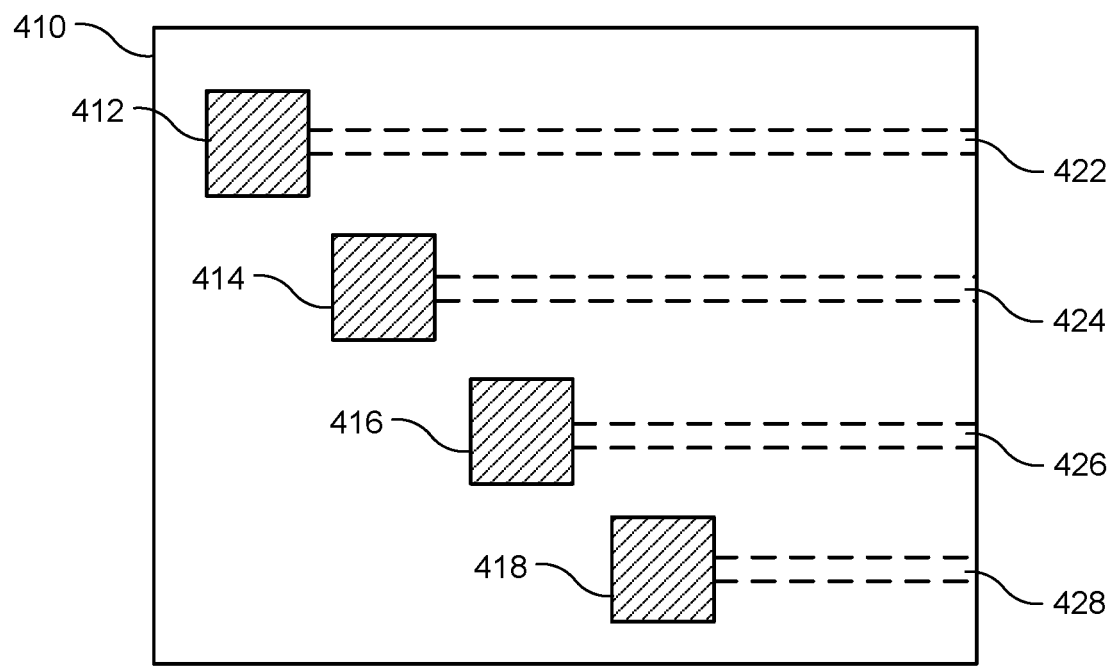
FIGS. 4A and 4B illustrate an apparatus for manufacturing a multi-analyte sensor, according to one embodiment.
Figure 4B:
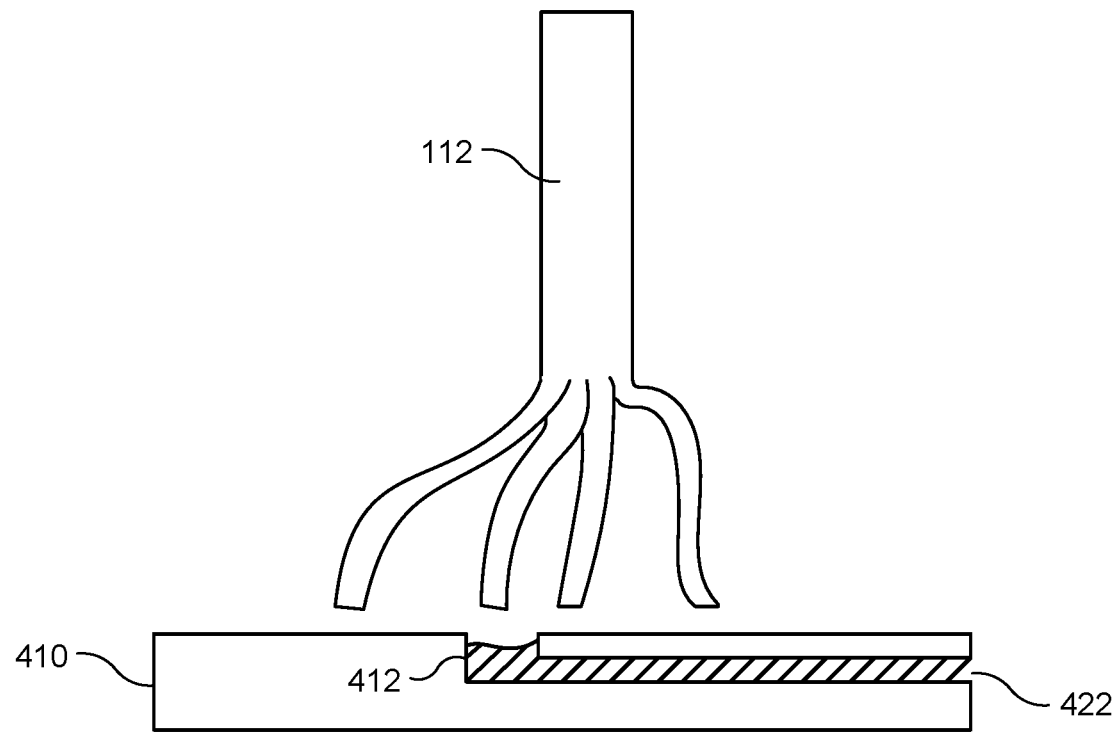

FIGS. 4A and 4B illustrate one embodiment of an apparatus for manufacturing a multi-analyte sensor 112. The manufacturing process enabled by the apparatus involves selectively dipping the strips of a sensor 112 one after another into wells containing liquid solutions of MIPs for the target analytes of the sensor. Alternatively, some or all of the strips may be dipped in liquid solutions of the MIPs simultaneously. Furthermore, in other embodiments, alternative manufacturing processes may be used for the sensor 112, such as 3D printing, spraying the MIPs onto the strips, or the like.

In the embodiment shown in FIGS. 4A and 4B, the apparatus includes a plate 410 with multiple wells for liquid solutions of MIPs for the analytes of interest. In the embodiment shown, the plate 410 includes a first well 412, a second well 414, a third well 416, and a fourth well 418. The first well 412 is connected to a first channel 422 that passes through the plate to provide a first MIP for detecting a first analyte from a source (not shown). Similarly, the second well 414 is provided a second MIP for detecting a second analyte via a second channel 424, the third well 416 is provided a third MIP for detecting a third analyte via a third channel 426, and the fourth well 418 is provided a fourth MIP for detecting a fourth analyte via a fourth channel 428. Thus, the apparatus is configured to produce a sensor 112 for detecting four different analytes.

In the embodiment shown, the wells are square and arranged along a diagonal line such that they are both horizontally and vertically offset. This may enable easy and reliable selection of a particular strip of the sensor 112 and a particular well (and thus a particular MIP). The sensor 112 may have the strips separated (e.g., by placing a separator tool between the strips). To apply the desired MIP to the desired strip, the sensor 112 may be rotated until the desired strip is aligned with the well containing the desired MIP in one axis and the plate 410 moved laterally until the target strip is directly over the well with the specific MIP. The strip is then dipped in the well, coating the exposed portion or portions of electrical lines with the specific MIP. In other embodiments, different shapes and alignments of well may be used.

Example Method of Calibrating a Multi-Analyte Sensor

Figure 5A:
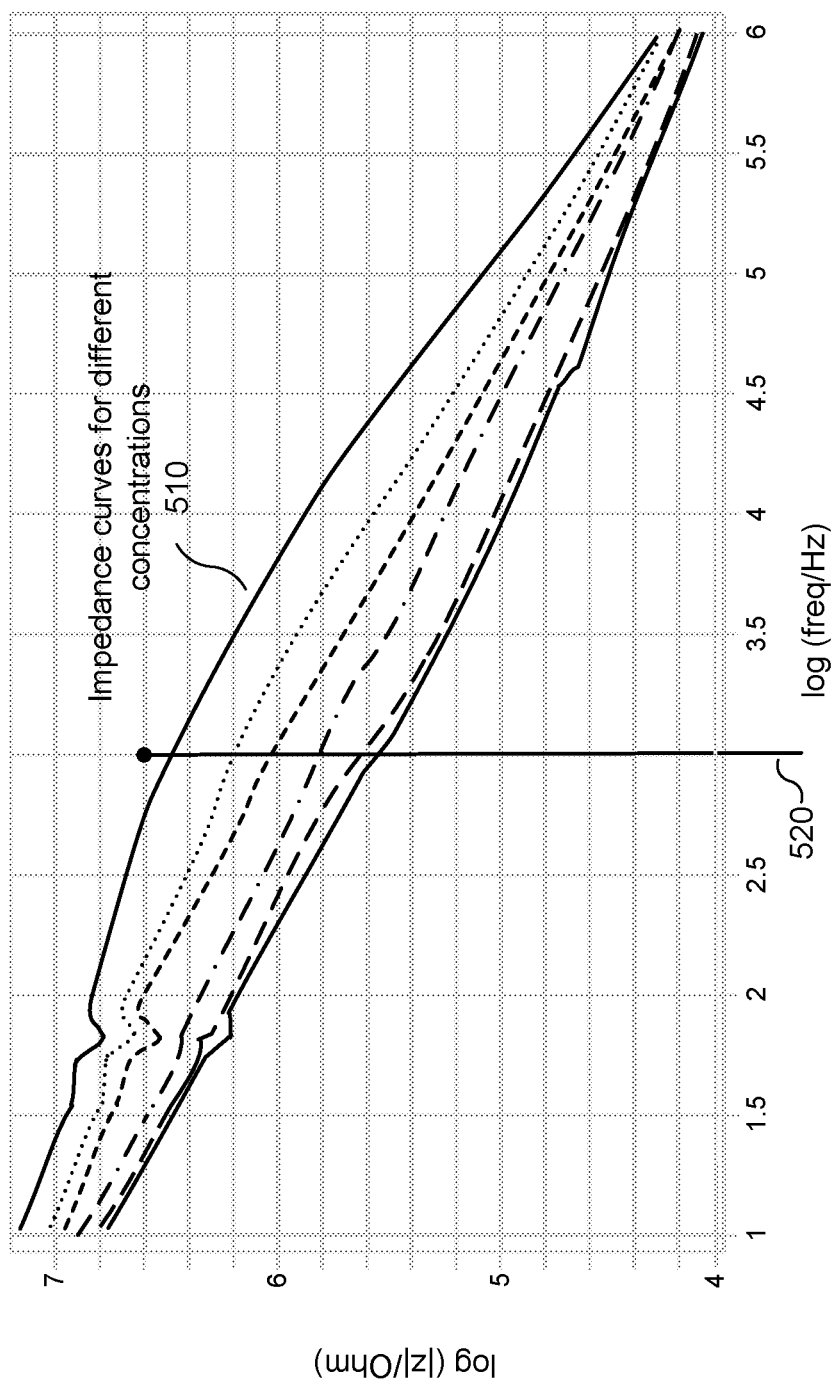
FIGS. 5A and 5B are plots illustrating a method for calibrating a multi-analyte sensor, according to one embodiment.
Figure 5B:
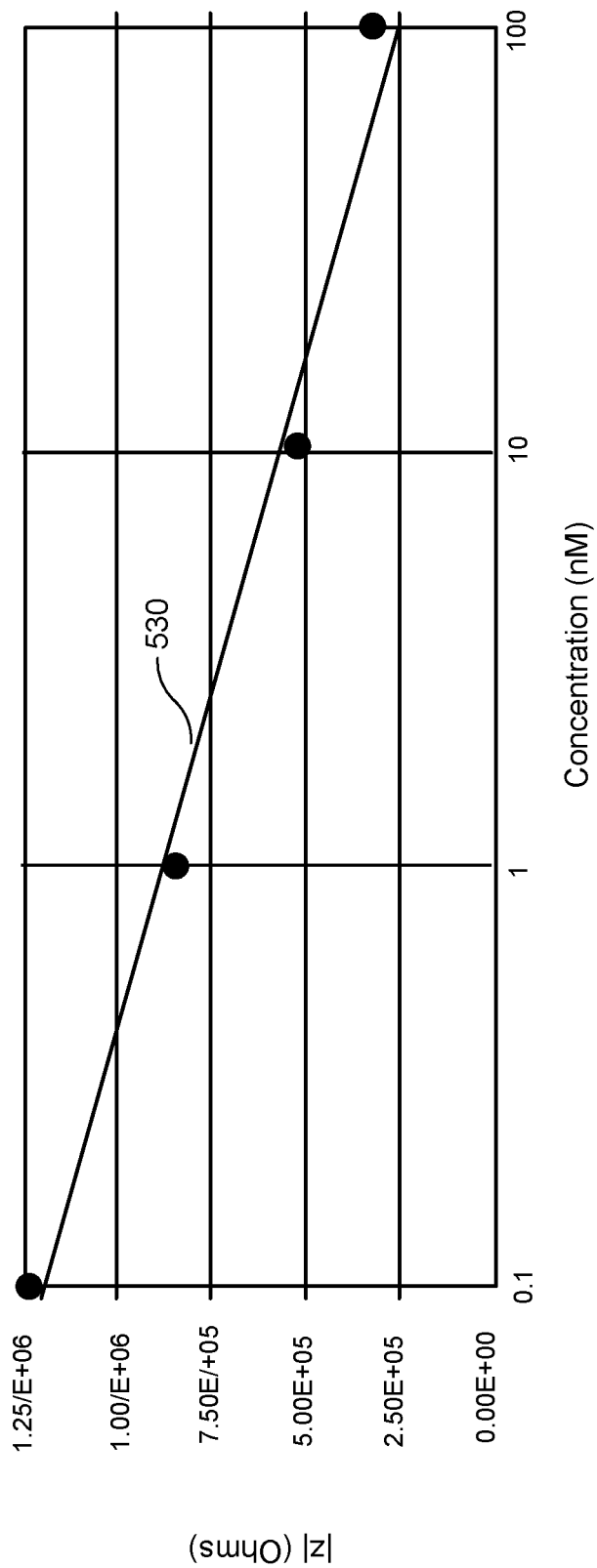

FIGS. 5A and 5B illustrate an example approach for calibrating the multi-analyte sensor 112. In a calibration phase, the variation of one or more electrical parameters of the sensor 112 with frequency is measured for a range of samples with known concentrations of a target analyte are measured. For example, in FIG. 5A, a set of six impedance curves 510 corresponding to six samples with differing concentrations of the target analyte are shown. Based on the log-log plot of impedance against frequency, a sampling frequency 520 is selected. The sampling frequency 520 may be selected using one or more criteria. For example, in one embodiment, the frequency with the largest impedance range is selected as the sampling frequency 520 to provide a good signal-to-noise ratio. In another embodiment, the frequency with the most linear response across the range of concentrations of interest for the target analyte or analytes is selected. Different sampling frequencies 520 may be selected for different analytes.

FIG. 5B is a plot of impedance against concentration of the target analyte at the target frequency, according to one embodiment. In FIG. 5B, a linear trend line 530 is fitted to the data points. Thus, in a measurement phase, the impedance measured for the electrical line or lines of the sensor 112 corresponding to the target analyte can be converted to a concentration of the target analyte using the trend line 530. Use of a linear trend line 530 has the advantage of simplicity, making it easy and computationally inexpensive to convert any measurement of impedance into the corresponding concentration. However, in other embodiments, non-linear calibration may be used, such as fitting a higher-order polynomial to the measured data points or using a lookup table with piecewise interpolation between the measured data points.

Although FIGS. 5A and 5B illustrate the calibration technique using impedance, a similar approach can be adopted for any electrical parameter of the sensor 112. The parameter may be measured for a range of concentrations at a range of frequencies to identify a sampling frequency and then a mapping (e.g., a trend line or lookup table) can be determined between the parameter and the concentration of the target analyte at the sampling frequency.

Additional Considerations

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Similarly, use of "a" or "an" preceding an element or component is done merely for convenience. This description should be understood to mean that one or more of the element or component is present unless it is obvious that it is meant otherwise.

Where values are described as "approximate" or "substantially" (or their derivatives), such values should be construed as accurate +/−10% unless another meaning is apparent from the context. From example, "approximately ten" should be understood to mean "in a range from nine to eleven."

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Upon reading this disclosure, those of skill in the art will appreciate still additional alternative structural and functional designs for a multi-analyte sensor as well as methods for making and using such a sensor. Thus, while particular embodiments and applications have been illustrated and described, it is to be understood that the described subject matter is not limited to the precise construction and components disclosed. The scope of protection should be limited only by the following claims.

What is claimed is:

1. A multi-analyte sensor comprising:
   a body having a proximal end and a distal end, the body comprising an electrical insulator;
   a first electrical conductor running through the body from the proximal end towards the distal end and through the electrical insulator, wherein the electrical insulator defines a first opening that exposes a portion of the first electrical conductor;
   a first molecular imprinted polymer (MIP) coating disposed on at least some of the portion of the first electrical conductor exposed by the first opening, the portion of the first electrical conductor exposed by the first opening being one of a plurality of exposed portions of the first electrical conductor exposed by a plurality of openings, defined by the electrical insulator, arranged along a top or bottom surface of the body, wherein an electrical property of the first MIP coating changes responsive to a concentration of a first target analyte to which the first MIP coating is exposed;
   a second electrical conductor running through the body from the proximal end towards the distal end and through the electrical insulator, wherein the electrical insulator defines a second opening that exposes a portion of the second electrical conductor; and
   a second MIP coating disposed on at least some of the portion of the second electrical conductor exposed by the second opening, wherein an electrical property of the second MIP coating changes responsive to a concentration of a second target analyte to which the second MIP coating is exposed.

2. The multi-analyte sensor of claim 1, further comprising an adaptor connected to the proximal end of the body and configured to couple the first and second electrical conductors to a controller.

3. The multi-analyte sensor of claim 1, wherein the body comprises a plurality of strips made at least partially from the electrical insulator and the first and second electrical conductors are embedded in corresponding ones of the plurality of strips.

4. The multi-analyte sensor of claim 1, wherein the portion of the second electrical conductor exposed by the second opening and coated with the second MIP coating is configured to have electrical properties that are substantially invariant with regard to concentration of the first target analyte.

5. The multi-analyte sensor of claim 3, wherein the plurality of strips each have a length between five microns and twenty centimeters and a width between one micron and five centimeters, and the plurality of strips are separated by between one micron and two centimeters.

6. The multi-analyte sensor of claim 3, wherein the portion of the first electrical conductor exposed by the first opening is at an end that is furthest from the body of a first strip of the plurality of strips.

7. The multi-analyte sensor of claim 3, wherein the plurality of openings are arranged along a first one of the plurality of strips in which the first electrical conductor is embedded.

8. The multi-analyte sensor of claim 1, further comprising a mask having a window configured to move relative to the body from a first position to a second position, wherein the window is aligned with the portion of the first electrical conductor exposed by the first opening in the first position and aligned with a different exposed portion of the plurality of exposed portions of the first electrical conductor in the second position.

9. The multi-analyte sensor of claim 1, wherein a second exposed portion of the plurality of exposed portions of the first electrical conductor is not coated in the first MIP and is directly exposed to an environment of the multi-analyte sensor.

10. The multi-analyte sensor of claim 1, wherein a third electrical conductor runs through the electrical insulator, the electrical insulator defining a third opening that exposes a portion of the third electrical conductor, the portion of the third electrical conductor exposed by the third opening being at least partially coated with the first MIP.

11. The multi-analyte sensor of claim 1, wherein the first target analyte is one of: cortisol, dehydroepiandrosterone (DHEA), melatonin, progesterone, estrogen, testosterone, cytokines, C-reactive protein, or cholesterol.

12. The multi-analyte sensor of claim 3, wherein the body, including the plurality of strips, is formed from a single cable, the strips separated by a plurality of longitudinal splits in the cable.

13. A multi-analyte sensing device comprising:
a multi-analyte sensor including:
a body having a proximal end and a distal end, the body comprising an electrical insulator;
a first electrical conductor running through the body from the proximal end towards the distal end and through the electrical insulator, wherein the electrical insulator defines a first opening that exposes a portion of the first electrical conductor;
a first molecular imprinted polymer (MIP) coating disposed on at least some of the portion of the first electrical conductor exposed by the first opening, the portion of the first electrical conductor exposed by the first opening being one of a plurality of exposed portions of the first electrical conductor exposed by a plurality of openings, defined by the electrical insulator, arranged along a top or bottom surface of the body, wherein an electrical property of the first MIP coating changes responsive to a concentration of a first target analyte to which the first MIP coating is exposed;
a second electrical conductor running through the body from the proximal end towards the distal end and through the electrical insulator, wherein the electrical insulator defines a second opening that exposes a portion of the second electrical conductor; and
a second MIP coating disposed on at least some of the portion of the second electrical conductor exposed by the second opening, wherein an electrical property of the second MIP coating changes responsive to a concentration of a second target analyte to which the second MIP coating is exposed; and a controller configured to:
receive output from the multi-analyte sensor indicating the electrical property of the first MIP coating and the electrical property of the second MIP coating;
determine a concentration of the first target analyte present in a sample based on the electrical property of the first MIP coating; and
determine a concentration of the second target analyte present in the sample based on an electrical property of the second electrical conductor.

14. The multi-analyte sensing device of claim 13, wherein the multi-analyte sensing device is a toothbrush.

15. The multi-analyte sensing device of claim 13, further comprising an adaptor connected to the proximal end of the body and configured to couple the first and second electrical conductors to the controller.

16. The multi-analyte sensing device of claim 13, wherein the portion of the second conductor exposed by the second opening and coated with the second MIP coating is configured to have electrical properties that are substantially invariant with regard to concentration of the first target analyte.

17. The multi-analyte sensing device of claim 13, wherein the body comprises a plurality of strips made at least partially from the electrical insulator and the first and second electrical conductors are embedded in corresponding ones of the plurality of strips, and the plurality of openings are arranged along a first one of the plurality of strips in which the first electrical conductor is embedded.

18. The multi-analyte sensing device of claim 13, further comprising a mask having a window configured to move relative to the body from a first position to a second position, wherein the window is aligned with the portion of the first electrical conductor exposed by the first opening in the first position and aligned with a different exposed portion of the plurality of exposed portions of the first electrical conductor in the second position.

19. The multi-analyte sensing device of claim 13, wherein a second exposed portion of the plurality of exposed portions of the first electrical conductor is not coated in the first MIP and is directly exposed to an environment of the multi-analyte sensor.

20. The multi-analyte sensing device of claim 13, wherein a third electrical conductor runs through the electrical insulator, the electrical insulator defining a third opening that exposes a portion of the third electrical conductor, the portion of the third electrical conductor exposed by the third opening being at least partially coated with the first MIP.

* * * * *